US008455566B2

(12) United States Patent
Anton et al.

(10) Patent No.: US 8,455,566 B2
(45) Date of Patent: Jun. 4, 2013

(54) MATERIALS LEADING TO IMPROVED DENTAL COMPOSITES AND DENTAL COMPOSITES MADE THEREFROM

(75) Inventors: Douglas Robert Anton, Wilmington, DE (US); Gary Delmar Jaycox, West Chester, PA (US); Yongqing Huang, Wilmington, DE (US)

(73) Assignee: E I du Pont de Nemours and Company, Wilington, DE (US)

( * ) Notice: Subject to any disclaimer, the term of this patent is extended or adjusted under 35 U.S.C. 154(b) by 430 days.

(21) Appl. No.: 11/974,772

(22) Filed: Oct. 16, 2007

(65) Prior Publication Data
US 2009/0105370 A1    Apr. 23, 2009

Related U.S. Application Data

(60) Provisional application No. 60/852,528, filed on Oct. 18, 2006.

(51) Int. Cl.
*A61K 6/083* (2006.01)
*A61C 5/00* (2006.01)
*C08G 18/10* (2006.01)

(52) U.S. Cl.
USPC ............ 523/117; 433/228.1; 528/59; 528/75; 106/35

(58) Field of Classification Search
USPC ................... 523/117; 433/228.1; 528/59, 75
See application file for complete search history.

(56) References Cited

U.S. PATENT DOCUMENTS

| | | | |
|---|---|---|---|
| 3,825,518 A | 7/1974 | Foster et al. | |
| 3,931,678 A | 1/1976 | O'Sullivan et al. | |
| 4,110,184 A | 8/1978 | Dart et al. | |
| 4,182,829 A | 1/1980 | Walkowiak et al. | |
| 4,243,578 A | 1/1981 | O'Sullivan et al. | |
| 4,400,159 A | 8/1983 | Orlowski et al. | |
| 4,691,045 A | 9/1987 | Fukuchi et al. | |
| 4,952,241 A | 8/1990 | Reiners et al. | |
| 5,177,120 A | 1/1993 | Hare et al. | |
| 6,017,973 A * | 1/2000 | Tamura et al. | 522/96 |
| 6,353,041 B1 * | 3/2002 | Qian | 523/116 |
| 6,653,375 B2 | 11/2003 | Moszner et al. | |
| 2002/0082315 A1 | 6/2002 | Moszner et al. | |
| 2006/0258771 A1 | 11/2006 | Anton et al. | |

FOREIGN PATENT DOCUMENTS
WO    WO 01/95862 A1    12/2001

OTHER PUBLICATIONS

Buonocore et al., "Synthesis and Properties of Certain Urethanes of Potential Use in Restorative Dentistry", New York State Dental Journal, vol. 35, Mar. 1969, pp. 135-147.
Watts et al., "Kinetic Measurements of Photo-Polymerization Contraction in Resins and Composites", Meas. Sci. Technol., 2, 1991, pp. 788-794.
Atai et al., "Synthesis, Characterization, Shrinkage and Curing Kinetics of a New Low-Shrinkage Urethane Dimethacrylate Monomer for Dental Applications", Dental Materials, 23, 2007, pp. 1030-1041.

* cited by examiner

*Primary Examiner* — Tae H Yoon
(74) *Attorney, Agent, or Firm* — Kevin S. Dobson

(57) ABSTRACT

Provided herein are uncured dental composites suitable for, among other things, filling cavities in teeth.

9 Claims, No Drawings

MATERIALS LEADING TO IMPROVED DENTAL COMPOSITES AND DENTAL COMPOSITES MADE THEREFROM

CROSS-REFERENCE TO RELATED APPLICATION

This application claims priority under 35 U.S.C. §119 from U.S. Provisional Application Ser. No. 60/852,528 filed on Oct. 18, 2006.

FIELD OF THE INVENTION

This invention relates to composite materials for restorative dentistry. More particularly, it relates to new components for dental composites that impart an attractive combination of good mechanical properties and low shrinkage.

BACKGROUND OF THE INVENTION

In recent years, composite materials comprising highly filled polymers have become commonly used for dental restorations. Current composite materials contain crosslinking acrylates or methacrylates, inorganic fillers such as glass or quartz, and a photoinitiator system suitable for curing by visible light. Typical methacrylate materials include 2,2'-bis[4-(2-hydroxy-3-methacryloyloxypropyl)phenyl]propane ("Bis-GMA"); ethoxylated Bisphenol A dimethacrylate ("EBPDMA"); 1,6-bis-[2-methacryloyloxyethoxycarbonylamino]-2,4,4-trimethylhexane ("UDMA"); dodecanediol dimethacrylate ("$D_3MA$"); and triethyleneglycol dimethacrylate ("TEGDMA"). The structural formulae for these are shown below.

Dental composite materials offer a distinct cosmetic advantage over traditional metal amalgam. However, they do not offer the longevity of amalgam in dental fillings. The primary reason for failure is excessive shrinkage during photopolymerization in the tooth cavity, which can cause leakage and bacterial reentry. Another reason is they have inadequate strength and toughness, as reflected in the measured properties of flexural strength and fracture toughness. Hence, there is still a need for new monomers and new monomer combinations which, when polymerized, impart high fracture toughness and flexural strength in the resulting composite. It is also highly desirable to have low shrinkage stress on polymerization.

WO 01/95862 A1 summarizes several teachings from the prior art. The first teaching is that, while it is known that increasing the molecular weight of the monomers used in making a composite decreases the polymerization shrinkage of the composite, using higher molecular weight monomers undesirably increases viscosity. The prior art has taught the use of low viscosity reactive diluents such as TEGDMA when the desired monomers are too viscous to make a good composite. However these reactive diluents typically have very high polymerization shrinkages and they compromise the properties of the final composite.

One of the more common commercially used monomers is Bis-GMA. However, it is highly viscous at room temperature and difficult to work with. It is therefore diluted with a second, lower viscosity polymerizable component ("fluidizer"), a methacrylate monomer, such as TEGDMA, tetraethylene glycol dimethacrylate, or dodecanediol dimethacrylate. However, while providing low viscosity, lower viscosity components (generally low molecular weight monomers) can

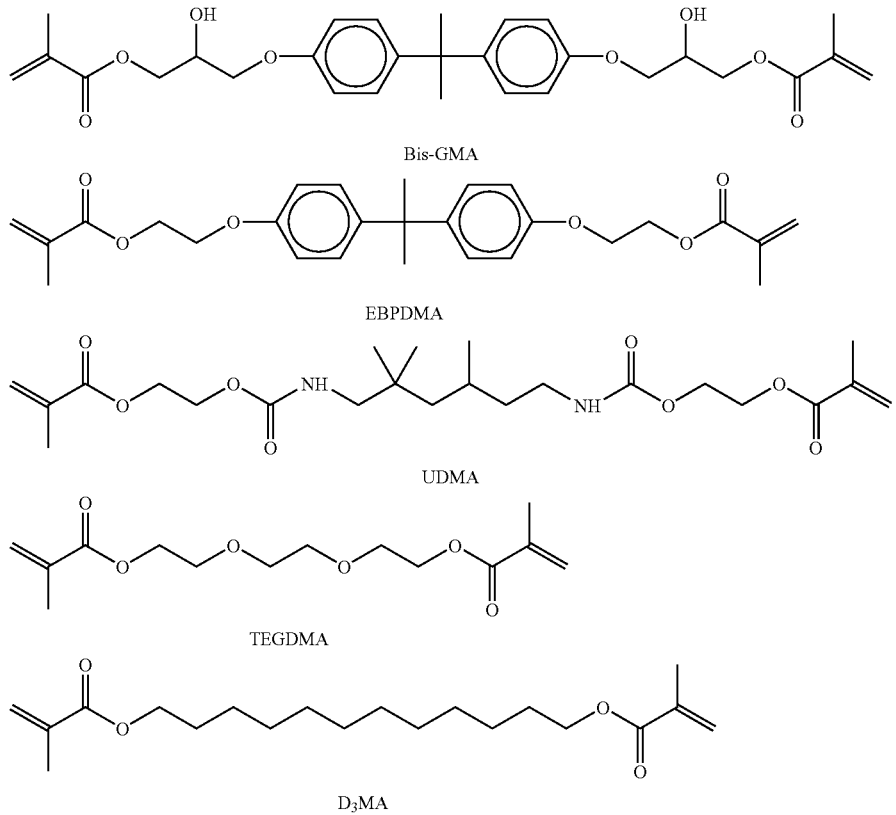

contribute to increased shrinkage. Increasingly, Bis-GMA and TEGDMA have been combined with UDMA and EBPDMA, but shrinkage remains high enough that improvement is desirable.

Urethane (meth)acrylates are common constituents of curable adhesives, coatings, printing inks and dental materials. One monomer employed frequently in the dental field is 7,7,9-trimethyl-4,13-dioxo-3,14-dioxa-5,12-diazahexadecan-1,16-diyldimethacrylate (UDMA). UDMA is prepared by the reaction of one mole of 2,2,4-trimethylhexamethylene diisocyanate with two moles of 2-hydroxymethyl methacrylate (HEMA) and is a viscous liquid at room temperature. UDMA is a relatively small molecule, with a mass per double bond near 235 Daltons. When employed as a major component in light-curable dental composite formulations, UDMA can lead to unacceptably high levels of polymerization shrinkage that ultimately compromise the durability and performance of the cured restorative.

In addition to UDMA, other urethane based dimethacrylates have been disclosed. For example, M. G. Buonocore and C. A. Casciani (New York State Dental Journal 1969, 35, 135) describe the reaction products of two moles of HEMA with one mole each of 2,4-toluoylene diisocyanate, naphthylene diisocyanate, hydrogenated diphenylmethane diisocyanate or hexamethylene diisocyanate. However, these products are crystalline compounds that require the use of liquid comonomers for the formulation of suitable dental composites.

U.S. Pat. No. 6,653,375 B2 discloses a series of urethane dimethacrylates for use in dental composites that are based on 1,3-bis(1-isocyanato-1-methylethyl)benzene ("TMXDI"). The urethanes described in this patent have (meth)acrylate arms one to eight carbon atoms long, optionally interrupted by oxygen atoms.

U.S. Pat. No. 4,243,578 relates to a series of urethane dimethacrylates prepared from the reaction of diisocyanate starting materials with $C_{1-8}$-hydroxyalkyl methacrylates and their use in dental filling materials.

U.S. Pat. No. 4,400,159 discloses the reaction of diisocyanates with 3-methylacroyl-2-hydroxypropyl esters to give highly branched urethane dimethacrylate analogues with short connecting arms, typically two carbon atoms and two oxygen atoms long, for use in dental restorative formulations.

U.S. Pat. No. 4,110,184 discloses the reaction of urethane containing pre-polymers with hydroxyalkyl (meth)acrylates and the use of these materials for the formulation of dental filling compositions. Short arms, two carbon atoms long, connecting the (meth)acrylate group and the urethane core are preferred.

U.S. Pat. No. 3,931,678 describes urethane (meth)acrylate monomers formed from the reaction of an organic polyisocyanate with a polymerizable (meth)acrylate ester containing reactive hydroxyl or amine groups, and the use of such materials in dental filling compositions. In this case the connecting arms are limited to alkyl chains of eight carbons or less.

U.S. Pat. No. 4,952,241 discloses (meth)acrylic acid derivatives containing urethane groups prepared by the reaction of di-(meth)acrylic acid esters with diisocyanates, followed by subsequent reactions with polyols, and the use of these compounds in dental materials.

Dental impression materials that are reaction products formed from di- or tri-isocyanates with a combination of dihydroxy and unsaturated monohydroxy reagents are described in U.S. Pat. No. 4,182,829.

U.S. Pat. No. 4,691,045 discloses particular (meth)acrylate oligomers and their use in making unsaturated urethanes that can be used for curable coatings and adhesive compositions.

U.S. Pat. No. 3,825,518 discloses the use of urethane di(meth)acrylates as monomers for dental filling materials wherein the connecting arms for the (meth)acrylate to the urethane core is an alkylene group. Preferred materials have the alkylene group containing 2 to 10 carbon atoms.

The dental composites that have been made using the urethane (meth)acrylates described in the above references do not sufficiently meet the need for efficient and effective monomers for dental composite materials that combine reduced shrinkage with sufficiently low viscosity, high polymerization rate, and acceptable mechanical properties. We have found that the urethane (meth)acrylate monomers described herein, having relatively long, conformationally flexible arms, instead of short arms as previously taught, meet this need.

SUMMARY OF THE INVENTION

In its first aspect, the present invention is an uncured dental composite material comprising (a) a composition comprising at least one compound of the formula:

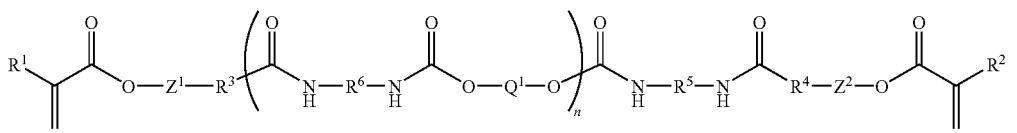

wherein:

n=0 to 5;

$R^1$ and $R^2$ are each independently H or methyl;

$R^5$ and $R^6$ are independently selected divalent organic radicals, each comprising 1-20 carbon atoms;

each $Q^1$ is independently selected and is a divalent organic radical comprising 1-50 carbon atoms;

$Z^1$ and $Z^2$ are each independently selected and are represented by the formula

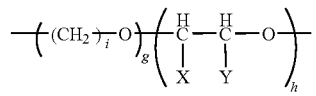

wherein i=2-10;

g and h are each independently 0 or 1, with the proviso that at least one of g and h is nonzero; and X and Y are each independently H or a $C_1$-$C_4$ alkyl group;

$R^3$ and $R^4$ are each independently selected and are represented by the formula

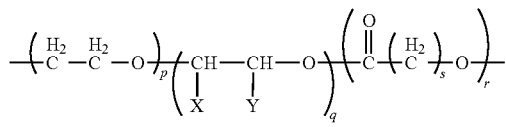     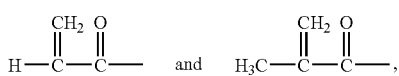

respectively.

wherein X and Y are as defined above, p, q, and r are each independently 0-50, with the provisos that at least one of q or r must be nonzero if p is nonzero, that s is 2 to 10, and that the total number of in-chain carbon atoms must be greater than or equal to 9.

(b) at least 10 wt % radioopaque filler; and (c) a polymerization initiator.

In another aspect, the present invention is the uncured dental composite described above, wherein component (a) consists essentially of at least one compound of Formula I, wherein n=0.

In yet another aspect, the present invention is an uncured dental composite material comprising a composition comprising at least one compound of Formula I, at least one polymerization initiator compound, at least one filler, and at least one additional polymerizable (meth)acrylic ester not of Formula I.

DETAILED DESCRIPTION OF THE INVENTION

In the context of this application, a number of terms are utilized.

The term "dental composite material" as used herein denotes a composition that can be used to remedy natural or induced imperfections in, or relating to, teeth. Examples of such materials are filling materials, reconstructive materials, restorative materials, crown and bridge materials, inlays, onlays, laminate veneers, dental adhesives, teeth, facings, pit and fissure sealants, cements, denture base and denture reline materials, orthodontic splint materials, and adhesives for orthodontic appliances. The term "uncured dental composite material" specifically refers to such material before it is subjected to a curing process.

As used herein, the term "isocyanate" means a compound containing the univalent radical —NCO.

As used herein, the term "urethane" denotes a compound containing the divalent radical —NH—CO—O—.

As used herein, the term "alkyl" means a univalent group derived from an alkane by removing a hydrogen atom from any carbon atom: —$C_nH_{2n+1}$ where $n \geq 1$.

As used herein, the term "alkylene" means the divalent radical derived from an alkane by removing two hydrogen atoms: —$C_nH_{2n}$— where $n \geq 1$.

As used herein, the term "carbocyclic" means having or relating to or characterized by a ring composed of carbon atoms.

As used herein, the terms "(meth)acrylic," "(meth)acrylyl" and "(meth)acrylate" refer to both methacrylic and acrylic, to methacrylate and acrylate, and to methacrylyl and acrylyl, respectively.

As used herein, the terms "acrylyl" and "methacrylyl" refer to the univalent radicals As used herein, the term "polymerizable (meth)acrylic ester component" means one or more materials that bear (meth)acrylate groups, such that the materials are capable of undergoing free radical polymerization.

As used herein, the term "arm" denotes, in the urethane (meth)acrylates described herein, a linear segment connecting a urethane group to a (meth)acrylyl group. A "long" arm comprises at least 11 in-chain carbon atoms. An "in-chain" atom is one atom in a linear covalently bonded assembly of atoms.

As used herein, the term "diol" means an organic compound having two hydroxyl (—OH) groups per molecule.

As used herein, the term "caprolactone" means ε-caprolactone, CAS Registry # 502-44-3:

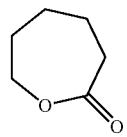

As used herein, the term "1,4-cyclohexanedimethanol" refers to the material designated by CAS Registry # 105-08-8:

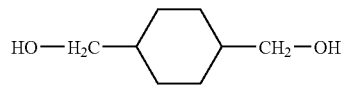

As used herein, the word "comprise" or "comprising," when used to describe a composition, means that the composition contains the recited component(s), but may include other components not recited.

As used herein, the expression "consists essentially of," when used to describe a composition, means that the composition contains the recited component(s), but may include trace quantities of impurities that do not have a substantial effect on the function of the component(s) that is/are recited.

Where a range of numerical values is recited herein, unless otherwise stated, the range is intended to include the endpoints thereof, and all integers and fractions (provided the context allows) within the range.

Urethane (meth)acrylates

The present invention provides a dental composite material comprising a composition comprising at least one urethane methacrylate compound of the Formula I,

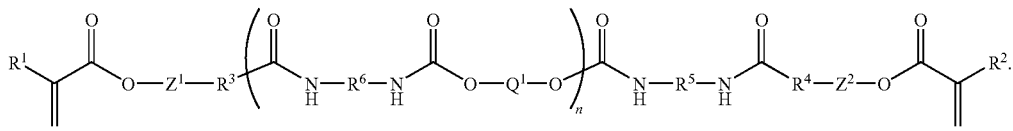

wherein: n=0 to 5; $R^1$ and $R^2$ are each independently H or methyl;

$R^5$ and $R^6$ are independently selected divalent organic radicals, each comprising 1-20 carbon atoms;

each $Q^1$ is independently selected and is a divalent organic radical comprising 1-50 carbon atoms;

$Z^1$ and $Z^2$ are each independently selected and are represented by the formula

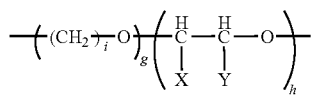

wherein i=2-10;

g and h are each independently 0 or 1, with the proviso that at least one of g and h is nonzero; and X and Y are each independently H or a $C_1$-$C_4$ alkyl group;

$R^3$ and $R^4$ are each independently selected and are represented by the formula

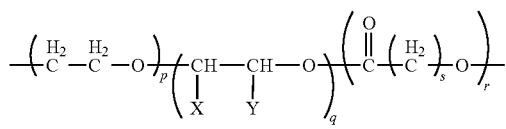

wherein X and Y are as defined above, p, q, and r are each independently 0-50, with the provisos that at least one of q or r must be nonzero if p is nonzero, that s is 2 to 10, and that the total number of in-chain carbon atoms must be greater than or equal to 9.

The "arms" of the compound of Formula I are the $Z^1$—$R^3$ and $Z^2$—$R^4$ segments.

It is preferred that $R^1$ and $R^2$ are each methyl.

It is preferred that $R^5$ and $R^6$ are each independently selected from the group of divalent radicals consisting of a. 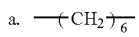

b. 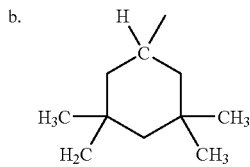

c. 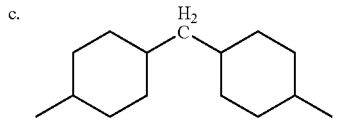

-continued d. 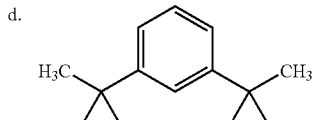

e. 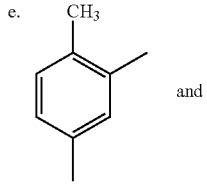 and f. 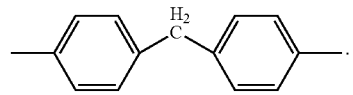.

Preferably, each $Q^1$ is a divalent organic radical comprising 1 or more rings, for example,

 and 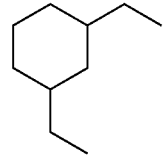

More preferably, each $Q^1$ is a divalent organic radical comprising both 1 or more rings and at least one in-chain ether or ester group, for example,

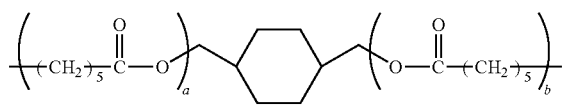

which can be prepared by the method described in U.S. Pat. No. 5,159,047 wherein a and b are each independently an integer in the range of 0 to 6 and a+b=2-6.

Another preferred Q' divalent radical is

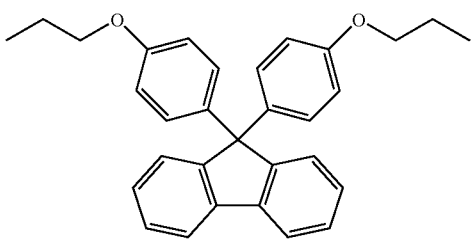 [SMILES: CCCOc1ccc(C2(c3ccc(OCCC)cc3)c3ccccc3-c3ccccc32)cc1]

Examples of compounds of Formula I include without limitation:

UM-1: wherein n=1-5; $R^1$ and $R^2$ are each methyl; for groups $Z^1$ and $Z^2$, g=0, i=0, h=1 and X and Y are each H; for groups $R^3$ and $R^4$, p=0, q=0, r=15 and s=5; and $R^5$ and $R^6$ are each

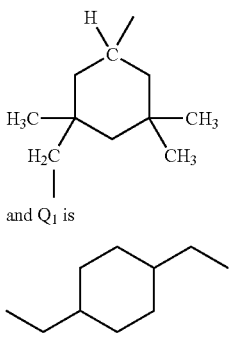

and $Q_1$ is

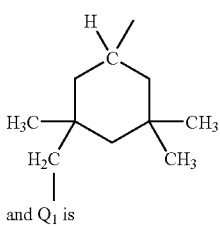

UM-2: wherein n=1-5; $R^1$ and $R^2$ are each methyl; for groups $Z^1$ and $Z^2$ g=0, i=0, h=1, X and Y are either H or methyl, providing that X and Y are not the same; for groups $R^3$ and $R^4$, p=0, q=1-11, r=0, s=0, X and Y are either H or methyl, providing that X and Y are not the same; and $R^5$ and $R^6$ are each

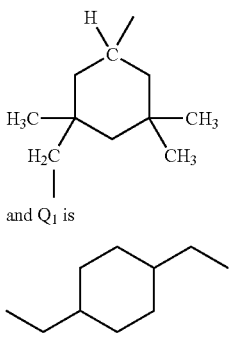

and $Q_1$ is

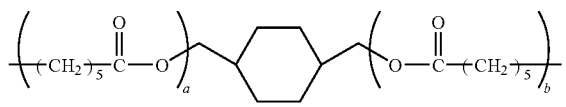

wherein a and b are each independently an integer in the range of 0 to 6 and a+b=2-6.

UM-3: wherein n=1-5; $R^1$ and $R^2$ are each methyl; for groups $Z^1$ and $Z^2$ g=0, i=0, h=1, X and Y are either H or methyl, providing that X and Y are not the same; for groups $R^3$ and $R^4$, p=0, q=1-11, r=0, s=0, X and Y are either H or methyl, providing that X and Y are not the same; and $R^5$ and $R^6$ are each

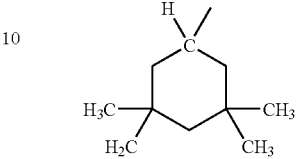

and $Q_1$ is

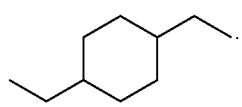

The present invention provides dental composite materials comprising a composition comprising at least one urethane (meth)acrylate compound of Formula I. A subset of the urethane (meth)acrylate compounds of Formula I are those wherein n=0, i.e., compounds of Formula II:

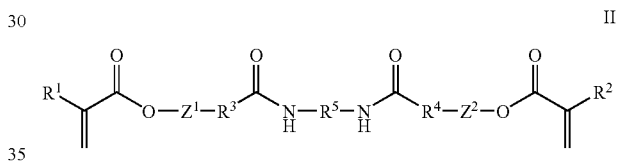

wherein $R^1$, $R^2$, $R^3$, $R^4$, $R^5$, $Z^1$ and $Z^2$ are as described above.

Examples of compounds of Formula II include without limitation:

UM-4: wherein $R^1$ and $R^2$ are each methyl; for groups $Z^1$ and $Z^2$, g=0, i=0, h=1 and X and Y are each H; for groups $R^3$ and $R^4$, p=0, q=0, r=1-5, and s=5; and $R^5$ is

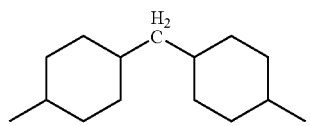

UM-5: wherein $R^1$ and $R^2$ are each methyl; for groups $Z^1$ and $Z^2$ g=0, l=0, h=1, X and Y are either H or methyl, providing that X and Y are not the same; for groups $R^3$ and $R^4$, p=0, q=1-11, r=0, s=0, X and Y are either H or methyl, providing that X and Y are not the same; and $R^5$ is

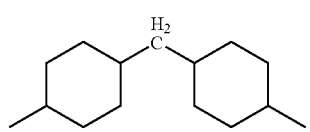

UM-7: wherein $R^1$ and $R^2$ are each methyl; for groups $Z^1$ and $Z^2$, g=0, i=0, h=1 and X and Y are each H; for groups $R^3$ and $R^4$, p=0, q=0, r=1-5, and s=5; and $R^5$ is

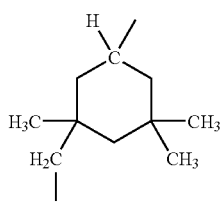

Urethane (meth)acrylate dental composite material containing compounds of Formula I may also be made using mixed (meth)acrylic esters. In one such example, $R^1$ and $R^2$ are each methyl and $R^5$ is an equimolar mixture of

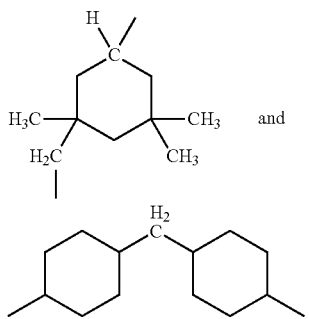

and

For half of the arms, including the terminal (meth)acrylate group, in groups $Z^1$ and $Z^2$, g=0, i=0, h=1 and X and Y are each H; for groups $R^3$ and $R^4$, p=0, q=0, r=1-5 and s=5. For the other half of the arms, including the terminal (meth)acrylate group, in groups $Z^1$ and $Z^2$, g=0, i=0, h=1, and X and Y are either H or methyl, providing that X and Y are not the same; in groups $R^3$ and $R^4$, p=0, q=1-11, r=0, s=0, and X and Y are either H or methyl, providing that X and Y are not the same.

These urethane (meth)acrylate compounds are produced by reacting isocyanates or isocyanate oligomers with hydroxy-containing (meth)acrylate monomers to make urethane methacrylates.

Urethane (meth)acrylate compounds of Formula I wherein n=0-5 can be made by a process comprising the steps:
(a) charge a reaction vessel with the desired ratio of the selected diol(s) and diisocyanate(s),
(b) heat to 40-120° C. with stirring under a dry-air flow over a two to six hour period,
(c) add hydroxy-containing (meth)acrylate(s) dropwise over a 10 minute to two hour period,
(d) discontinue reaction when the consumption of the isocyanate endgroups is judged to be complete based on IR spectroscopy or isocyanate titration, and
(e) cool reaction product to room temperature.

This synthetic scheme will typically make a mixture of compounds of Formula I with variation in the value of n in the formula.

Urethane (meth)acrylate compounds of Formula II can be made by a process comprising the steps:
(a) charge a reaction vessel with desired diisocyanate(s) and catalyst (preferably dibutyltin dilaurate),
(b) heat to 70-100° C. with stirring under a dry-air flow,
(c) add hydroxy-containing (meth)acrylate(s) dropwise over a 30 minute to two hour period,
(d) discontinue the reaction when the consumption of the isocyanate reagent is judged to be complete based on IR spectroscopy or isocyanate titration, and
(e) cool the reaction product to room temperature.

Typical polymerization catalysts that are useful in the above processes include, but are not limited to, dibutyltin dilaurate, dibutyltin diacetate, $Sn(2-ethylhexanoate)_2$, $Sn(n-octanoate)_2$; p-toluenesulfonic acid; and methanesulfonic acid. Tin(II) catalysts are preferred.

Isocyanates that can be used to make the urethane (meth)acrylates described herein include, but are not limited to, 4,4'-methylenebis(cyclohexyl) isocyanate, isopherone diisocyanate, and hexamethylene diisocyanate ("HMDI"). Isopherone diisocyanate is commercially available as Desmodur I® from Bayer MaterialScience LLC (Pittsburgh, Pa.).

Isocyanate oligomers that can be used to make the urethane (meth)acrylates described herein include, but are not limited to, oligomers formed from isopherone diisocyanate and 1,4-cyclohexanedimethanol; oligomers formed from isopherone diisocyanate and 1,4-cyclohexanedimethanol-caprolactone adducts; and mixtures of these.

Hydroxy-containing (meth)acrylate monomers that can be used to make the urethane (meth)acrylates described herein include, but are not limited to, polycaprolactone-2-(methacryloyloxy)ethyl ester; polypropylene glycol monomethacrylates; and polypropylene glycol-co-ethylene glycol monomethacrylates.

We have found that the urethane (meth)acrylate monomers described herein, having relatively long, conformationally flexible arms, instead of short arms as previously taught, have both high molecular weight per double bond, which typically results in lower shrinkage, and relatively low viscosity, which increases ease of handling. These monomers are useful in making dental composites often without the need for reactive diluents that are needed with many short-armed urethane di(meth)acrylate monomers. These long-armed monomers retain the excellent mechanical properties that are characteristic of urethane (meth)acrylate based composites and have improved shrinkage and handling characteristics. The combination of the higher molecular weight per double bond of the monomers and the reduced need for reactive diluents because of the relatively low viscosity allows the formation of superior dental composites. This can be demonstrated by a comparison of the relative handling values of composites made with long-armed monomers such as UM-4 and UM-5 versus the composite made with the short-armed monomer UM-6 (see Examples 23, 24, 25 (Comparative) in Table 1).

Additional Polymerizable (meth)acrylic Esters

As is well known to those skilled in the art, there are many attributes which must be introduced when formulating a dental composite. Introducing all of these attributes with only one monomer can be difficult, so it is common to use more than one monomer in the composition. Therefore in addition to compounds of Formula I, other polymerizable (meth)acrylic esters not of Formula I may be present in the uncured dental composite material. These additional polymerizable (meth)acrylic ester compounds may include both monofunctional compounds and polyfunctional compounds, where "monofunctional" denotes a compound having one (meth)acrylic group and "polyfunctional" denotes a compound having more than one (meth)acrylic ester group. The choice of which polymerizable (meth)acrylic ester(s) to add will depend on all of the desired attributes of the resulting composite, such as ease of handling, appearance, mechanical strength, refractive index, and the like.

Examples of polyfunctional (meth)acrylic ester compounds include, without limitation, 2,2'-bis[4-(2-hydroxy-3-methacryloyloxypropyl)phenyl]propane ("Bis-GMA");

ethoxylated Bisphenol A dimethacrylate ("EBPDMA"); 1,6-bis-[2-methacryloyloxyethoxycarbonylamino]-2,4,4-trimethylhexane ("UDMA"); dodecanediol dimethacrylate ("D$_3$MA"); triethyleneglycol dimethacrylate ("TEGDMA"); 1,1,1-tri[4-2-methyl-2-methacryloxyethoxy)-phenyl]ethane ("THPE PO MA"); and butanedioic acid, ethylidynetris[4,1-phenyleneoxy(2-hydroxy-3,1-propanediyl)] tris[2-[(2-methyl-1-oxo-2-propenyl)oxy]ethyl]ester ("THPE GE Su-HEMA"), cyclohexanedimethanol-polycaprolactone dimethacrylate:

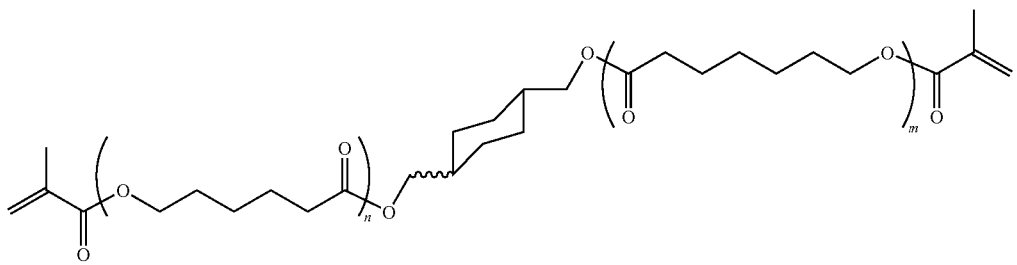

where n and m are both independently an integer from 0-10, (This compound, herein referred to as "DM-CL-CHDM," can be made from CL-CHDM by the process described in U.S. patent application Ser. No. 11/431,773.) and dimethacryloxy ethoxylated 9,9'-bis(4-hydroxyphenyl) fluorene monomer ("DMEHBF").

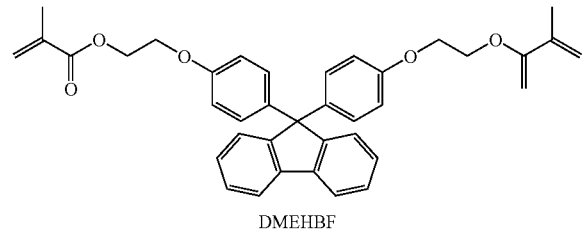 [SMILES: C=C(C)C(=C)OCCOc1ccc(C2(c3ccc(OCCOC(=O)C(=C)C)cc3)c3ccccc3-c3ccccc32)cc1]

DMEHBF

The synthesis of DMEHBF is described in Culbertson, B. M.; Tiba, A.; Sang, J.; Liu, Y. N., Polym. Adv. Technol. 1999, 10, 275-281.

One particular class of polymerizable (meth)acrylic ester that can be introduced is the class of polymerizable (meth) acrylic esters with a refractive index greater than that of the composition of Formula I used in the uncured dental composite.

In a preferred uncured dental composite, the compounds of Formula I (n=0 to 5) and the additional polymerizable (meth) acrylic ester(s) not of Formula I are used in a weight ratio of ranging from about 25:75 to 75:25. At this weight ratio, the viscosity of the uncured dental composite is low enough to allow fillers to be added and adequately mixed. The resulting material, when cured, shows relatively low shrinkage with good mechanical properties.

Polymerization Initiator Compounds

The composition of the present invention also comprises a polymerization initiator. Suitable polymerization initiator compounds include peroxy-type initiators such as benzoyl peroxide, dicumyl peroxide, lauryl peroxide, tributyl hydroperoxide, and other materials familiar to those skilled in the art. Azo-type initiators such as 2,2'-azobis(isobutyronitrile), 2,2'-azobis(2,4-dimethyl valeronitrile), 2,2'-azobis(2-methyl butane nitrile), and 4,4'-azobis(4-cyanovaleric acid) may also be used.

Preferred initiator systems are photoinitiators, i.e., initiator systems that are activated by light. One example is the photosensitizer camphorquinone used in conjunction with a tertiary amine like ethyl dimethylaminobenzoate or dimethylaminoethyl methacrylate as a co-initiator.

The polymerization initiator (optionally with a photosensitizer) can be used in the range of about 0.1 weight percent to about 5 weight percent, preferably about 0.2 weight percent to about 3 weight percent, and more preferably about 0.2 weight percent to about 2 weight percent. The percentages are based on the total weight of the uncured dental composite, exclusive of filler.

Fillers

The composition of the present invention also comprises at least 10 wt % of a radioopaque filler. One class of fillers that may be used in the uncured dental composites described herein is inorganic fillers. Among the preferred inorganic fillers are barium aluminum silicate, barium aluminum borosilicate, ytterbium trifluoride, glass beads, silica, quartz, borosilicates, alumina, alumina silicates, and strontium aluminum silicates. Mixtures of inorganic fillers may also be employed. The mean particle size of the inorganic fillers is preferably between about 0.1 and 15 μm.

Another class of fillers that may be used in the uncured dental composites described herein is organic fillers. Suitable organic fillers include prepolymerized fillers ("prepolymerized" in the sense that organic monomers have been polymerized to produce an organic resin, which, optionally, can be ground, prior to their inclusion in the uncured dental composites of this invention). Such prepolymerized fillers may be included in the uncured dental composites described herein alone or in combination with an inorganic filler. These prepolymerized fillers can also optionally contain inorganic fillers such as those described above.

The total amount of filler in the uncured dental composites described herein can range from about 10 weight percent to about 90 weight percent, preferably from about 40 weight percent to about 90 weight percent, and more preferably from about 50 weight percent to about 85 weight percent. The percentages are based on the total weight of the uncured dental composite.

Additional Optional Ingredients

In addition to the components described above, the composite material may contain additional, optional ingredients. These may comprise activators, pigments, stabilizers, rheology control agents, antioxidants, and other materials.

The uncured dental composite material described herein can be prepared using any mixing means known in the art. Such methods include, but are not limited to, roll mills, vibratory mixers, sigma mixers, planetary mixers, SpeedMixers™ (from Flack Tek, Inc., Landrum, S.C.), extruders, Buss Kneaders (Coperion Holding GmbH, Stuttgart, Germany), and Brabender Plasticorders® (Intellitorque, Brabender, Hackensack, N.J.).

The dental composite materials of the present invention can be used to fill cavities in teeth. Other treatments may include preventative, restorative, or cosmetic procedures in teeth. Typically, without limiting the method to a specific order of steps, the dental composite materials are placed on dental tissue, either natural or synthetic, cured, and shaped as necessary to conform to the target dental tissue. Dental tissue includes, but is not limited to, enamel, dentin, cementum, pulp, bone, and gingiva.

The dental composite materials may also be useful as dental adhesives, primers, bonding agents, pit and fissure sealants, cements, denture base and denture reline materials, orthodontic splint materials, and adhesives for orthodontic appliances. The materials also may be useful for making bridges, crowns, inlays, onlays, laminate veneers, and facings. The materials of the invention also may be useful for prosthetic replacement or repair of various hard body structures such as bone and also may be useful for reconstructive purposes during surgery, especially oral surgery.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "h" means hour(s), "min" means minute(s), "mL" means milliliter(s), "m" means meter(s), "cm" means centimeter(s), "mm" means millimeter(s), "µm" means micrometer(s), "g" means gram(s), "mol" means mole(s), "mmol" means millimoles, "RPM" means revolutions per minute, "wt %" means weight percent(age), "mW" means milliwatt(s), "MPa" means megapascal(s), "d50" means 50% of particles have a diameter below a given size, "NMR" means nuclear magnetic resonance spectroscopy, "IR" means infrared spectroscopy, "TEGDMA" means triethylene glycol dimethacrylate, "CQ" means camphorquinone, "EDB" means ethyl 4-dimethylaminobenzoate, "MEHQ" means 4-methoxyphenol, and "6-EO" means ethoxylated(6) bisphenol A.

Materials

Desmodur I® isopherone diisocyanate and dicyclohexylmethane diisocyanate were obtained from Bayer MaterialScience LLC (Pittsburgh, Pa.). Poly-propylene glycol monomethacrylate was provided by The Sartomer Company (Exton, Pa.). 4-Hydroxybutyl methacrylate, 4-methoxyphenol ("MEHQ"), poly-caprolactone 2-(methacryloyloxy)ethyl ester, and dibutyltin dilaurate were obtained from Aldrich Chemical Company (Milwaukee, Wis.). Caprolactone was obtained from Dow Chemical Company (Midland, Mich.). 1,4-cyclohexanedimethanol (CAS #105-08-8, Eastman product code # CHDM-D) was obtained from Eastman Chemical Company (Kingsport, Tenn.), Triethylene glycol dimethacrylate ("TEGDMA") was obtained from EssTech (Essington, Pa.), product code product code X 943-7424, inhibited with hydroquinone (50-70 ppm). Photosensitizers were obtained from Aldrich Chemical Company (Milwaukee, Wis.): camphorquinone (97%, catalogue #12, 489-3) and ethyl 4-dimethylaminobenzoate (99+%, catalogue #E2, 490-5). Aerosil® OX-50 fumed silica was obtained from Degussa (Dusseldorf, Germany). Schott 8235 UF1.5 glass powder was obtained from Schott AG (Mainz, Germany); it had a mean diameter, d50, of 1.5 µm and was treated with $C_{10}H_{20}O_5Si$ to a level of 2.3 wt % silane. Aerosil® R972 hydrophobic fumed silica was obtained from Degussa (Dusseldorf, Germany). Schott GM 27884 glass powder (d50=0.7 µm, 6 wt % silanized) was obtained from Schott AG (Mainz, Germany). Ethoxylated(6) bisphenol A ("6-EO") was obtained from the Sartomer Company (Exton, Pa.). CL-CHDM was prepared according to the method described in U.S. Pat. No. 5,159,047

Dental Composites Preparation

The composites were prepared by dissolving 1.3 wt % photoinitiator camphorquinone (CQ) and 2.6 wt % co-initiator ethyl 4-dimethylaminobenzoate (EDB) in selected monomer(s) in Table 1; then adding 20 wt % OX-50 fumed silica and 280 wt % silanized Schott 8235 glass (all weight percentages were based on the mass of monomers), with the exception of Example 10 in which 11.2 wt % silanized Schott 8235 glass was added with no fumed silica; and finally mixing all components by a DAC 150 FVZ-K FlackTek SpeedMixer™ (FlackTek Inc., Hauschild, Germany) at 3500 RPM for 30 seconds after the sample was stored in a 60 to 70° C. oven for about 10 min.

Test Methods

Mechanical Testing

The flexural strength test was based on ISO 4049. The fracture toughness test was based on both the ASTM polymers standard (ASTM D5045) and the ASTM ceramics standard (ASTM C1421, precracked beam method). Testing was conducted at a test speed of 0.5 mm/min at room temperature and ambient humidity using a three-point bend fixture (span to depth ratio of 10). The specimens were molded using the flexural bar mold specified in ISO 4049. The specimens were precracked halfway through their depth. Two modifications to the test procedures were made. The first was the use of smaller test specimens than those recommended in the ASTM C1421 standard (2 mm×2 mm×25 mm instead of the recommended minimum dimensions of 3 mm×4 mm×20 mm). The second was the use of a slitting circular knife to machine the precracks. The knife was 0.31 mm in thickness with a 90 single bevel. The modified test procedures produced precracks that were equivalent to precracks produced using the techniques recommended in ASTM D5045.

The uncured pastes were packed into a stainless steel mold (2 mm×2 mm×25 mm). The packed mold was sandwiched on either side with a Mylar® polyester sheet, followed a glass plate. The molded bars were cured in the mold by irradiating each exposed side for 1 minute using an array of three Spectrum® 800 dental lamps (DENTSPLY International, York, Pa.), each bearing an 8-mm light tip, at 800 mW/cm². Five bars were used for each of the fracture toughness and flexural strength tests. The bars were stored in glass vials until use and conditioned in water for 24 h at 37° C., just prior to the tests.

Handling Test 0.2 mL of uncured paste was sandwiched between Mylar® polyester sheets which were then sandwiched between glass plates. This assembly was then subjected to a 5 kg load for 30 seconds. At the end of the test the diameter of the disk of composite was measured. The final handling number is calculated by the following equation:

$$\text{Handling scale} = \frac{\text{Average diameter of squashed disk} - 13 \text{ mm}}{1 \text{ mm}}$$

Shrinkage Measured by Linometry

Composite shrinkage was measured using linometer method, a modified Watts & Cash method (Watts, D. C., Cash, A. J., Kinetic measurements of photo-polymerization contraction in resins and composites. Meas. Sci. Technol. 1991, 2, 788-794.). Three samples per composite were tested. Approximately 0.35 g of sample material was pressed into a 12 mm diameter disk on a glass microscope slide by using a 15 mm diameter cover slip on the top. The thickness of the sample was about 1.4 mm. The original height ($H_o$) and the final height ($H_f$) at 2 min after curing were measured by a Mititoyo VL-50A Litematic, digital height indicator, i.e. a linometer. The sample was cured on the top for 2 min by a 13-mm Spectrum® 800 dental lamp (DENTSPLY International, York, Pa.), at 800 mW/cm². The shrinkage was calculated by the following equation:

$$\text{Shrinkage (\%)} = \frac{H_o - H_f}{H_o} \times 100\%$$

Example 1

Preparation of UM-1

16.2 g of 1,4-cyclohexanedimethanol was charged to a 250 mL round bottom flask equipped with a mechanical stirrer, addition funnel, and condenser. Desmodur I® isoperone diisocyanate, 50.0 g was added, and the mixture was heated to 50° C. and held for six hours to give a white, viscous, taffy-like material. The reaction mixture was allowed to cool overnight. The reaction mixture was then heated to 60° C., and 54.9 g of poly-caprolactone 2-(methacryloyloxy)ethyl ester was added over five minutes. The reaction mixture was then heated to 70° C. and held at that temperature for six hours. IR analysis showed the product contained no remaining isocyanate. The product was cooled to yield a clear glass.

Example 2

Preparation of UM-2

156.6 g of the CL-CHDM and 143.0 g of Desmodur I® isoperone diisocyanate were added to a 500 mL round bottom flask equipped with a mechanical stirrer, addition funnel, and condenser. The reaction mixture was heated to 70° C. for five hours under a dried air flow and then held at room temperature for 17 hours. The reaction mixture was re-warmed to 70° C., treated first with dibutyltin dilaurate (0.2 g) and then 235 g of poly-propylene glycol monomethacrylate was added over five minutes. The resulting reaction mixture was held at 70° C. for an additional fourteen hours and then cooled to yield a thick oil. IR analysis showed no isocyanate band.

Example 3

Preparation of UM-3

Desmodur I® isopherone diisocyanate (80 g, 0.36 mol) was charged into a 500 mL round bottom flask equipped with a mechanical stirrer, addition funnel and condenser. 1,4-Cyclohexanedimethanol (26 g, 0.18 mol) was added and the mixture heated to 78° C. for about one hour and then cooled overnight. The reaction mixture was re-heated to 76° C. under a dried-air flow, treated with dibutyltin dilaurate (two drops), and then poly-propylene glycol monomethacrylate (145 g, 0.39 mol) was added dropwise over a two hour period. The reaction mixture was heated with stirring for an additional hour at 70° C. At this point, IR analysis indicated the near complete consumption of reactive isocyanate.

Example 4

Preparation of UM-4

To a stirred solution of dicyclohexylmethane diisocyanate (50.0 g, 0.190 mol) and dibutyltin dilaurate (one drop) at 70° C. under dry air was added dropwise poly-caprolactone 2-(methacryloyloxy)ethyl ester (92.0 g, 0.378 mol) over a 60 minute period. The resulting reaction mixture was stirred at 70° C. under a dried-air flow for an additional 9 hours with some unreacted isocyanate reagent still present. Methanol (1.5 mL) was added and the reaction was heated at 70° C. for another five hours and then cooled to room temperature, giving the final product. IR spectroscopy of the final product showed a near absence of a peak near 2267 cm$^{-1}$ (NCO stretching) indicating the consumption of the dicyclohexylmethane diisocyanate reagent. Additionally, a strong signal near 3342 cm$^{-1}$ (urethane N—H stretching) and a weaker peak at 1637 cm$^{-1}$ (methacrylate double bond) were both noted in the IR spectrum.

Example 5

Preparation of UM-5

To a stirred solution of dicyclohexylmethane diisocyanate (30.0 g, 0.114 mol) and dibutyltin dilaurate (four drops) at 100° C. under dry air was added dropwise poly-propylene glycol monomethacrylate (83.5 g, 0.229 mol) over a 60 minute period. The resulting reaction mixture was stirred at 100° C. under a dried-air flow for an additional two hours and then cooled to room temperature, giving the final product. IR spectroscopy of the final product showed an absence of a peak near 2267 cm$^{-1}$ (NCO stretching) indicating the complete reaction of the dicyclohexylmethane diisocyanate reagent. Additionally, a strong signal near 3342 cm$^{-1}$ (urethane N—H stretching) and a weaker peak at 1637 cm$^{-1}$ (methacrylate double bond) were both noted in the IR spectrum. $^1$H NMR spectroscopy (in CDCl$_3$) confirmed the presence of terminal methacrylate groups in the final product, with vinylic proton resonances falling near 5.5 (1H) and 6.1 (1H) ppm.

Example 6 (Comparative)

Preparation of UM-6

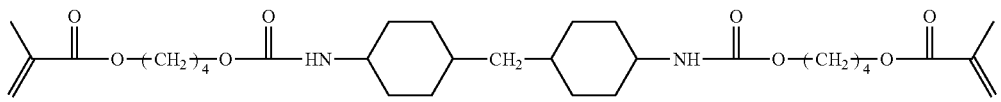

To a stirred solution of dicyclohexylmethane diisocyanate (78.7 g, 0.300 mol) and dibutyltin dilaurate (one drop) at 95° C. under dry air was added dropwise a solution of 4-hydroxybutyl methacrylate (95 g, 0.60 mol) and MEHQ (0.031 g, 0.25 mmol) over a 40 minute period. The resulting reaction mixture was stirred at 95° C. under a dried-air flow for a total of 8 hours and then cooled to room temperature, giving the final product. IR spectroscopy of the final product showed the near absence of a peak near 2267 cm$^{-1}$ (NCO stretching) indicating the consumption of the dicyclohexylmethane diisocyanate reagent. Additionally, a strong signal near 3350 cm$^{-1}$ (urethane N—H stretching) and a weaker peak at 1637 cm$^{-1}$ (methacrylate double bond) were both noted in the IR spectrum. $^1$H NMR spectroscopy (in CDCl$_3$) confirmed the presence of terminal methacrylate groups in the final product, with vinylic proton resonances falling near 5.5 (1H) and 6.1 (1H) ppm.

Example 7

Preparation of UM-7

Desmodur I® isopherone diisocyanate, 50 g was charged to a 250 mL round bottom flask equipped with a mechanical stirrer, addition funnel, and condenser. One drop of dibutyltin dilaurate was added, and the reaction was heated to 70° C. Poly-caprolactone 2-(methacryloyloxy)ethyl ester, 110.0 g, was added through the addition funnel over one hour. The reaction was heated at 70° C. for a total of 12 hours. IR analysis showed the presence of a minor N═C═O band. 0.5 mL of methanol was added and the heat was continued for one hour. The reaction was cooled to yield a thick oil with a Gardner-Holt viscosity of approx. Z-6.

Example 8

Preparation of Urethane Methacrylate Dental Composite Material Using Mixed Methacrylic Esters To a stirred solution of dicyclohexylmethane diisocyanate (30.0 g, 0.114 mol), Desmodur I® isopherone diisocyanate (36.8 g, 0.166 mol) and dibutyltin dilaurate (one drop) at 65° C. under dried-air was added dropwise a mixture of polypropylene glycol monomethacrylate (83.5 g, 0.229 mol) and poly-caprolactone-2-(methacryloyloxy)ethyl ester (77.6 g, 0.332 mol) over a 40 minute period. The resulting reaction mixture was stirred at 85° C. under a dried-air flow for a total of 8 hours and then cooled to room temperature, giving the final product. IR spectroscopy of the final product showed an absence of a peak near 2267 cm$^{-1}$ (NCO stretching) indicating the complete reaction of the isocyanate reagents. Additionally, a strong signal near 3350 cm$^{-1}$ (urethane N—H stretching) and a weaker peak at 1637 cm$^{-1}$ (methacrylate double bond) were both noted in the IR spectrum. $^1$H NMR spectroscopy (in CDCl$_3$) confirmed the presence of terminal methacrylate groups in the final product, with vinylic proton resonances falling near 5.5 (1H) and 6.1 (1H) ppm.

Example 9

A composite paste was prepared as described above except that 15 wt % Aerosil® R972 and 285 wt % Schott GM 27884 were used as fillers. The composite consisted of UM-1,6-EO and DMEHBF in a ratio of 50:25:25 by weight. The composite showed fracture toughness of 1.85 MPa·m$^{0.5}$, flexural strength of 122 MPa, shrinkage of 1.50% and handling value of 2.2.

Examples 10-25 (Comparative)

Uncured dental composite materials were prepared as described above using the monomers and proportions by weight described in Table 1. Shrinkage, flexural strength, fracture toughness, and handling were measured as described above. Results are presented in Table 1.

TABLE 1

| Example | Monomer Mixture (ratios by wt.) | Wt % filler | Shrinkage (%) | Flexural Strength MPa | Fracture Toughness MPa·m$^{1/2}$ | Handling |
|---|---|---|---|---|---|---|
| 10 | UM-1 | 10 | 1.54 | 102 | 2.82 | 5.3 |
| 11 | UM-2 | 75 | 1.26 | 41 | 0.55 | 5.6 |
| 12 | UM-1/UM-2 70/30 | 75 | 0.83 | 113 | 2.33 | 0.2 |
| 13 | UM-3/UM-2 50/50 | 75 | 1.38 | 48 | 0.76 | 5.2 |
| 14 | UM-1/UM-3 10/90 | 75 | 1.26 | 97 | 1.95 | 2.7 |
| 15 | UM-1/6-EO 60/40 | 75 | 1.64 | 152 | 2.64 | 4.6 |
| 16 | UM-1/DM-CL-CHDM 50/50 | 75 | 2.26 | 107 | 1.89 | 5.3 |
| 17 | UM-1/UM-5 70/130 | 75 | 1.09 | 118 | 1.71 | 1.4 |
| 18 | UM-2/DM-CL-CHDM 50/50 | 75 | 2.15 | 46 | 0.71 | 11.7 |
| 19 | UM-7 | 75 | 1.96 | 138 | 2.65 | 7.1 |
| 20 | Example 8 product | 75 | 2.03 | 76 | 1.51 | 9.6 |
| 21 | UM-7/DM-CL-CHDM 50/50 | 75 | 2.89 | 112 | 2.04 | 13.6 |
| 22 | UM-5/DM-CL-CHDM 50/50 | 75 | 2.55 | 59 | 0.85 | 14.7 |
| 23 | UM-4 | 75 | 1.91 | 135 | 2.36 | 5.3 |
| 24 | UM-5 | 75 | 2.00 | 63 | 1.06 | 11 |
| 25 (Comparative) | UM-6 | 75 | 1.23 | 91 | 1.17 | 2.5 |

We claim:

1. An uncured dental composite material comprising
   (a) a composition comprising at least one compound of the formula:

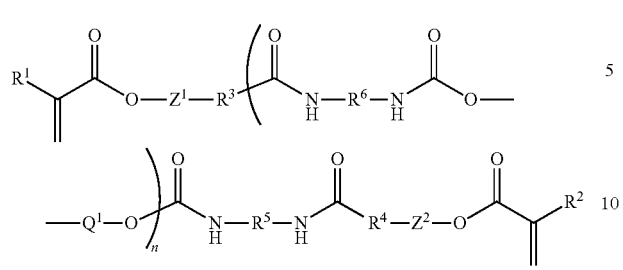

Formula I (b) at least 10 wt % radioopaque filler; and
(c) a polymerization initiator;
wherein with regard to Formula I:
  (i) n is in the range of from 1 to 5;
  (ii) $R^1$ and $R^2$ are each methyl;
  (iii) $Z^1$ and $Z^2$ are each independently selected and are represented by the formula

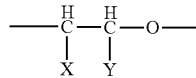

and
  (iv) $R^3$ and $R^4$ are each independently selected and are represented by the formula

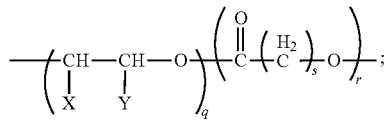

wherein:
  (A) for groups $Z^1$ and $Z^2$, X and Y are each H; for groups $R^3$ and $R^4$, q=0, r=1-5 and s=5; $R^5$ and $R^6$ are each

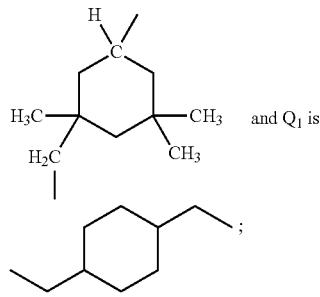

or
  (B) for groups $Z^1$ and $Z^2$, X and Y are either H or methyl, providing that X and Y are not the same; for groups $R^3$ and $R^4$, q=1-11, r=0, s=0, X and Y are either H or methyl, providing that X and Y are not the same; $R^5$ and $R^6$ are each

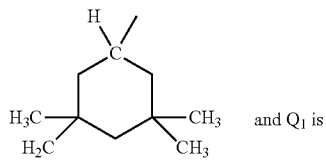

and $Q_1$ is

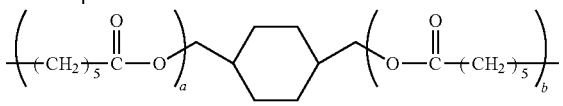

wherein a and b are each independently an integer in the range of 0 to 6 and a +b=2-6; or
  (C) for groups $Z^1$ and $Z^2$, X and Y are either H or methyl, providing that X and Y are not the same; for groups $R^3$ and $R^4$, q=1-11, r=0, s=0, X and Y are either H or methyl, providing that X and Y are not the same; $R^5$ and $R^6$ are each

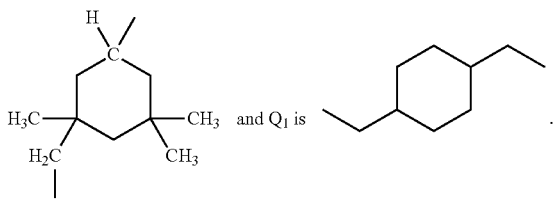

and $Q_1$ is

.

2. The uncured dental composite material of claim 1 further comprising at least one additional polymerizable (meth)acrylic ester not of Formula I.

3. The uncured dental composite material of claim 2 wherein the additional polymerizable (meth)acrylic ester not of Formula I is a difunctional (meth)acrylate monomer.

4. The uncured dental composite material of claim 3 wherein the additional polymerizable (meth)acrylic ester(s) not of Formula I has a refractive index greater than the refractive index of the composition comprising at least one compound of Formula I.

5. The uncured dental composite material of claim 3 wherein the difunctional (meth)acrylate monomer is 2,2'-bis[4-(2-hydroxy-3-methacryloyloxypropyl)phenyl]propane.

6. The uncured dental composite material of claim 3 wherein the difunctional (meth)acrylate monomer is dimethacryloxy ethoxylated 9,9'-bis(4-hydroxyphenyl) fluorene monomer.

7. The uncured dental composite material of claim 3 wherein the difunctional (meth)acrylate monomer is ethoxylated Bisphenol A dimethacrylate.

8. The uncured dental composite material of claim 7 further comprising dimethacryloxy ethoxylated 9,9'-bis(4-hydroxyphenyl) fluorene monomer.

9. A dental restoration article that is made by forming and curing the uncured dental composite material of claim 1.

* * * * *